United States Patent [19]

Poler

[11] 4,257,521

[45] Mar. 24, 1981

[54] PACKAGING MEANS FOR AN INTRAOCULAR LENS

[76] Inventor: Stanley Poler, 78 E. Second St., New York, N.Y. 10003

[21] Appl. No.: 94,912

[22] Filed: Nov. 16, 1979

[51] Int. Cl.³ .............. B65D 81/18; B65D 41/58; A61F 1/16; A61F 1/18
[52] U.S. Cl. ............................ 206/5.1; 206/205; 206/525; 220/23; 3/13
[58] Field of Search ........... 206/5.1, 210, 205, 525, 206/526, 527; 3/13; 220/23

[56] References Cited

U.S. PATENT DOCUMENTS

| | | | |
|---|---|---|---|
| 2,615,448 | 10/1952 | Fields | 220/23 |
| 3,822,780 | 7/1974 | Ulmer et al. | 206/205 |
| 4,113,088 | 9/1978 | Binkhorst | 206/210 |
| 4,149,279 | 4/1979 | Poler | 206/5.1 |
| 4,173,281 | 11/1979 | Trought | 206/5.1 |

*Primary Examiner*—William T. Dixson, Jr.
*Attorney, Agent, or Firm*—Hopgood, Calimafde, Kalil, Blaustein & Lieberman

[57] ABSTRACT

The invention contemplates an autoclavable mounting and package for an intraocular lens of the variety which is an assembly of a lens element and one or more lens-retaining haptic elements. The mounting in a preferred form comprises a single stiffly compliant sheet which is folded at one end, so that an upper panel can be detachably secured in register with a lower panel, there being coacting formations of the registering panels whereby the lens can be supported by and between the panels and via the haptic structure of the lens assembly.

10 Claims, 5 Drawing Figures

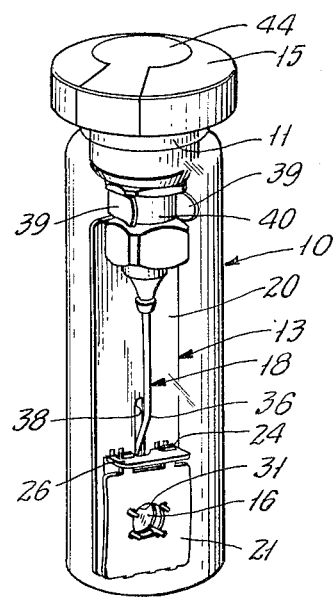
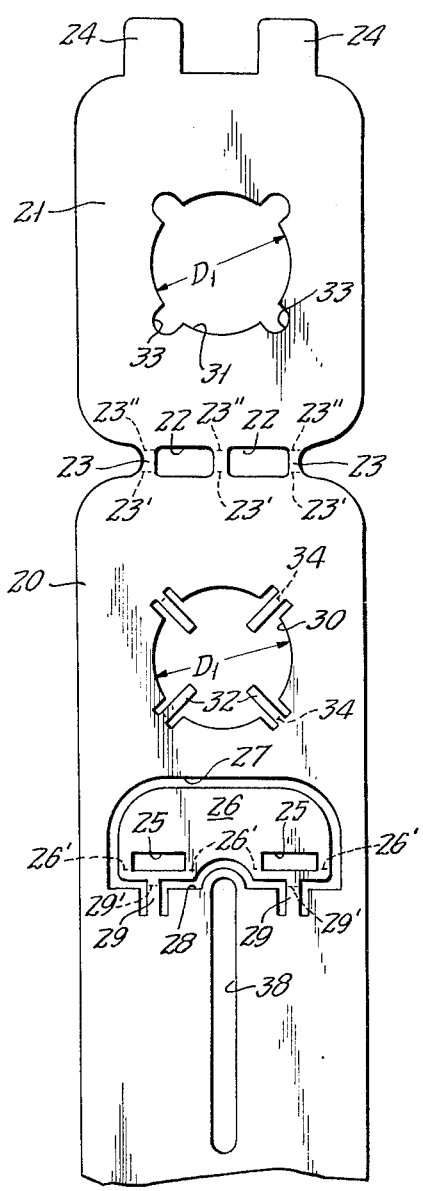
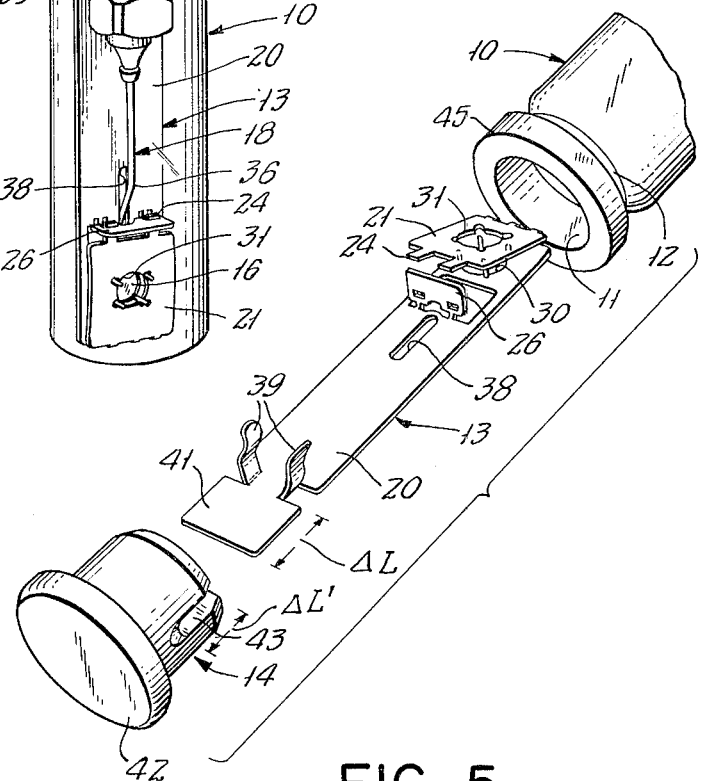
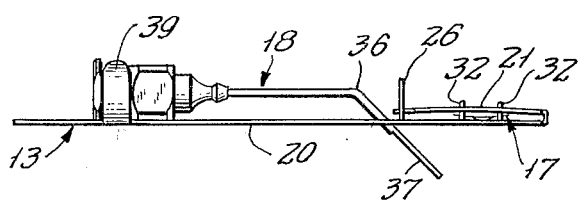
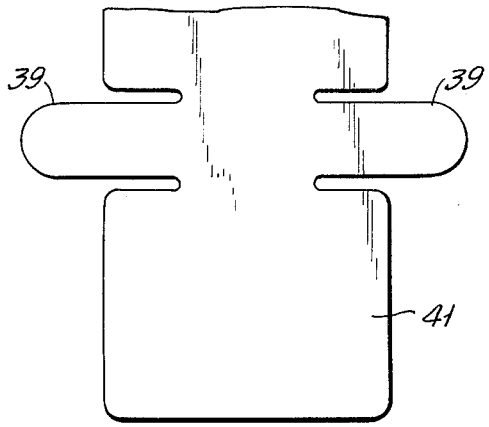
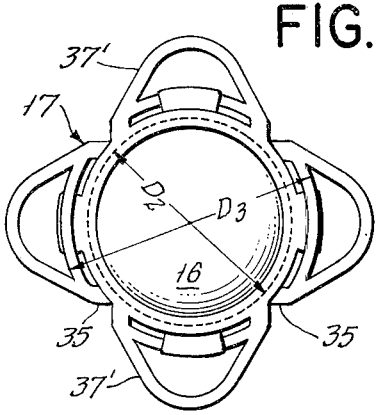

PACKAGING MEANS FOR AN INTRAOCULAR LENS

BACKGROUND OF THE INVENTION

The invention relates to means for the safe and efficient packaging of an intraocular-lens assembly, to permit shipment and storage, with instant utmost readiness for operative implantation of the lens assembly within a human eye.

In the variety of intraocular lenses wherein separate haptic structure is relied upon to circumferentially engage and support a lens element within an eye, it is vital that the assembly be safely and securely retained after manufacture, to permit instant availability for surgical implantation. And for those assemblies which rely upon optically finished glass for the lens element, there is a particular problem of safety against damage from mechanical shock. My U.S. Pat. No. 4,122,556 discloses one form of package whereby a manipulating tool is assembled to the haptic structure, so that the lens assembly is retained via the mounting of the tool. But this type of package lacks the security required to resist mechanical shock from all directions, and this type of package is limited as to the variety of haptic configurations to which it is adaptable.

BRIEF STATEMENT OF THE INVENTION

It is an object of the invention to provide improved packaging and mounting means of the character indicated.

Another object is to provide such structure which is fully autoclavable, with the lens assembly retained therein.

A further object is to provide such structure which is inherently resistant to mechanical shock, whatever the direction of the shock, and which isolates the lens element from supporting contact other than via its assembled haptic.

It is also an object to meet the above objects with structure which additionally accommodates the shock-resistant autoclavable mounting of a manipulating tool to be used by the surgeon in operative implantation of the packaged lens assembly.

A still further object is to provide a packaging mount for such lens and haptic assemblies, with inherent capability to mount an expanded variety of configurations.

The foregoing and other objects and features are realized by a preferred form of the invention wherein a single piece mount of relatively stiffly compliant sheet material, such as stainless steel, is bent and folded at one end such that an integral spring hinge is defined between an elongate lower generally rectangular panel and a shorter upper generally rectangular panel. The panels have detachable engagement to retain their folded relation of overlapping registry, and within their region of registry they have coacting formations to receive and locate an inserted lens and haptic assembly, the latter being supported only via the haptic, i.e., without contact with the lens element. The lower panel may include provision for removable support of a manipulative tool, and the entire loaded mount is resiliently retained against end-shake displacement within a glass-bottle container.

DETAILED DESCRIPTION OF PREFERRED EMBODIMENT

The preferred embodiment of the invention will be described in connection with the accompanying drawings, in which:

FIG. 1 is a perspective view of a complete and sealed package of the invention, with a sterilized lens assembly, mount and manipulating tool contained therein;

FIG. 2 is a plan view of the blank for the mount of FIG. 1;

FIG. 3 is a partly-broken, exploded, perspective view of mount and container elements of FIG. 1;

FIG. 4 is a simplified plan view of a typical lens and haptic assembly retained by the mount of FIG. 1; and FIG. 5 is a side view in elevation of the mount of FIGS. 1 and 3, in assembled retaining relation with an intraocular lens and haptic assembly.

The package of the invention is shown as comprising an elongate generally cylindrical container such as a glass bottle 10 having a sufficiently open mouth 11 at a neck 12 at one longitudinal end. An elongate mount 13 is removably insertable through the mouth opening and is resiliently retained in place by an elastomeric plug 14 and seal cap 15. An intraocular lens assembly, comprising a lens element 16 and circumferentially engaging haptic structure 17 (FIG. 4) is removably retained at the lower end of mount 13, and a manipulative tool 18 is removably retained at the upper end of mount 13. The mount 13 in general comprises an elongate lower rectangular panel 20 integrally joined at its lower end to a shorter rectangular upper panel 21, via a connecting hinge region which enables limited compliant articulation between an open condition (FIG. 3) and a closed position (FIG. 5) of substantial overlapping registry with the lower end of panel 20. Various integral formations of the mount 13 enable releasably locked engagement of panels 20-21 in their closed position, and releasable retention of the tool 18. These formations will be better understood by additional reference to the blank of FIG. 2, which accounts for the entire structure of mount 13.

The blank of FIG. 2 is of relatively stiffly compliant autoclavable material such as stainless steel, and although it may be cut by conventional stamping dies, it is my preference that it be effectively cut to all contours by photo-etch techniques analogous to those I have employed for manufacture of lens-supporting haptic structures. Such technique is described, for example, in my U.S. Pat. No. 4,080,709.

In the contouring which is shown, a transverse alignment of one or more slots 22 establishes a plurality of transversely spaced short connections 23 at which upper panel 21 is folded up and over lower panel 20, the normal unstressed relation of the parts being the slightly open or ajar relation depicted in FIG. 3; to make the indicated fold, I prefer to employ two equally crimped bends at longitudinally spaced alignments 23'-23'' at opposite ends of the connections 23, whereby gently compliant flexing between the open (FIG. 3) and closed (FIG. 5) positions of panels 20-21 may be uniformly distributed among and along all connections 23. Releasable latch formatitons to retain the closed position of FIG. 5 include one or more projecting latch lugs 24 at the free end of upper panel 21, and a corresponding number of matching latch-receiving slotted openings 25 in a latch-retaining lug 26, effectively struck up from the body of lower panel 20. A generally horseshoe shaped slot 27 establishes the outline of lug 26, and a generally U-shaped slot 28 between the legs of slot 27 establishes relatively narrow elongate and gently compliant bendable connections 29 of lug 26 to panel 20; again, I prefer to employ two equally crimped bends at longitudinally spaced alignments 29'–26', to avoid excessive stress or damage at any single location, and to provide a substantial fraction of the length of connections 29 for uniformly distributed compliant bending accommodation to manipulated articulation of lug 26 with respect to its normal latch-retaining position.

When panels 20–21 are in their latched position (FIG. 5), they retain a lens assembly such as that shown in FIG. 4. To this end, panels 20–21 have registering circular openings 30–31 of a diameter $D_1$ which is preferably in excess of the diameter $D_2$ of lens element 16, but the diameter $D_1$ is preferably less than the outer diameter $D_3$ of the circumferentially extending portion of the haptic structure 17, thereby assuring possible circumferential retention of the lens assembly solely via haptic engagement. To further assure such engagement by establishing concentricity of haptic and lens suspension with respect to the circular openings 30–31, plural upstanding locating prongs or lugs 32 are effectively struck out of panel 20 at the periphery of opening 30, and registering lobes 33 are formed at spaced locations on the periphery of opening 31. The crimpring-bend axis 34 for each lug 32 is at sufficient radial offset from the geometrical circle of opening 30, that the struck-up lugs 32 will at all times be radially outside this circle, and such that when panels 20–21 are in closed position (FIG. 5), the lugs 32 will enter and clear the lobes 33. Also, when thus struck up, the lugs 32 will be understood to have non-interfering but nevertheless concentricity-locating relation with corresponding locating-contour formations, such as the spaced peripheral notches shown at 35 for the illustrative haptic 17 of FIG. 4.

The manipulative tool 18 which is shown additionally carried by mount 13 may be of a variety generally as shown and described in my U.S. Pat. No. 4,122,556. It suffices here to note that it is a specially formed hypodermic needle having a base fitting for selective attachment to a syringe (not shown) containing saline solution to be discharged in the course of an implant procedure. The dispensing end of the needle is bent at 36, and a cylindrical half of the bent end is ground off, at 37, to define a stabilizing reference for engagement with opposed leg formations of the haptic 17, as at formations 37', when using the tool to manipulate the assembly 16–17. For detachable retention of tool 18, the lower panel 20 includes an elongate slot 38 adjacent the latching lug 26, for through-passage and location of the bent end 36 of the needle, and a pair of opposed rounded spring fingers 39 are effectively struck up from panel 20, for firm detachable resilient engagement with the body portion 40 of the base fitting of tool 18. Preferably, the location of fingers 39 is at least at a predetermined offset $\Delta L$ from the upper end of panel 20, thus defining an otherwise uncharacterized rectangular end region 41 of panel 20.

As previously noted, the plug 14 is of elastomeric material, selected for autoclavability, as for example a silicone variety made by the West Company, Phoenixville, Pennsylvania. It has a flanged outer end 42 for compressional seating against the rim of the bottle mouth 11, and the other end of its body has a diametrically extending slot formation 43 of depth $\Delta L'$ and which is preferably less than $\Delta L$ which receives and locates the end region 41 of panel 20. Closure is effected by formed application of the peripheral seal cap 15, which is shown to be of the variety having a center tab 44 which is finger-engageable, for elevation and tear off, to break the seal for once-only access to the contents of the container. When sealed by cap 15, it will be understood that a formed skirt edge of cap 15 engages over the bead 45 at the open end of bottle 10, to retain strong axial compression of flange 42 and to drive plug 14 into resiliently loaded compression of panel 20 against the bottom wall of bottle 10—the bottle, plug and panel (20) dimensions having been selected to achieve this result.

In use, the sealed package of the invention is fully autoclavable and thus retains sterility. In the operating room, the cap seal 15 is broken and plug 14 removed, thus exposing end region 41 for pinched manual grasp, to remove mount 13 and its removable articles. The tool 18 is then fitted to a syringe, and access to the lens assembly is afforded by simple finger deflection of lug 26 away from the position of FIG. 5 and to the point of latch release. The characterized trip 37 of tool 18 is then manipulated to engage the openings of both opposed haptic legs 37', and the lens assembly can now be freed from confinement by the retaining prong lugs 32, being then directly usable in an implant procedure.

The described packaging system will be seen to have met all stated objects, and to provide immediately usable tool and implant structure, upon seal-breakage in the operating room. Sterility and correct haptic assembly, and freedom from concern as to lens clipping, are assured, once the product has been assembled to its package, sealed and sterilized.

While the invention has been described in detail for the preferred form shown, it will be understood that modifications may be made without departure from the scope of the invention.

What is claimed is:

1. Packaging means for a circular intraocular lens in assembled relation to retaining haptic which has effective circumferential engagement to both axial sides of the periphery of the lens and which also extends radially outside the lens periphery and which also has external locating-edge formations at a geometrical circle which is concentric with but larger than the periphery of the lens, said packaging means comprising a snap-retaining holder formed from a single piece of compliant autoclavable sheet material, said piece comprising an elongate generally rectangular lower panel integrally and bendably connected along a transverse fold axis at one end to a generally rectangular but less elongate upper panel, detachably engageable interlocking formatitons at the free end of said upper panel and at that lower panel region with which said free end registers when bent to overstand said lower panel, said panels having circular apertures which register when said panels are thus bent, a plurality of angularly spaced haptic-locating lugs struck up from the body of one of said panels at locations angularly spaced about the circular aperture of said one panel and extending in the direction of the other panel, the circular aperture of said other panel having radially outward lobe recesses at locations registering with the struck-up lug locations and sized to allow clear passage of said lugs when said panels are thus bent, said lugs being adapted to engage the locating-edge formations of the haptic of a lens assembly, and said panels having axial-end retaining contact with the lens assembly via the haptic thereof when said formations are detachably engaged.

2. The packaging means of claim 1, wherein the sheet material is stainless steel.

3. The packaging means of claim 1, in which the diameter of said circular apertures is substantially the diameter of said geometrical circle, whereby the entire lens of the lens assembly is retained concentric to and wholly within the geometrical cylinder defined by and extending between said apertures.

4. The packaging means of claim 1, and including an elongate container bottle having a mouth adapted to receive longitudinal insertion of said packaging means, and bottle-closure means including an elastomeric plug having friction engagement within said mouth, said plug having a transverse panel-engaging slot open toward the inner volume of said bottle and extending axially to the extent that when said plug is fully inserted into the bottle mouth said lower panel is resiliently retained by the bottom of said plug, and means retaining said plug in panel-retaining position.

5. The packaging means of claim 1, and including an elongate container bottle having a mouth adapted to receive longitudinal insertion of said packaging means, and bottle-closure means including an elastomeric plug removably engageable with said mouth, said plug including a radially outward flange at its outer end, said flange having seating engagement with the adjacent axial end of the bottle when said plug is in panel-retaining relation.

6. The packaging means of claim 5, wherein said retaining means includes a frangible circumferential clamp band compressing said plug flange to the mouth of said bottle.

7. The packaging means of claim 1, in which that portion of said lower panel which extends beyond the detachable connection to said upper panel includes a struck up snap-retaining formation for detachable mounting of a manipulating tool for removal and operative manipulation of the assembled lens and haptic.

8. The packaging means of claim 1, in which said sheet material has a transversely extending slot at the fold axis, thereby effectively locally reducing the stiffness of the compliance of said sheet material at the fold axis.

9. The packaging means of claim 1, in which said interlocking formations comprise at least one longitudinally extending latch-lug formation at the free end of said upper panel, and a latch-retaining lug formation struck up from said lower panel at longitudinal register with said latch-iug formation when the apertures of said upper and lower panels are in register.

10. The packaging means of claim 9, in which said latch-retaining lug formation has a transverse slot in which said latch-lug formation is enterable to retain a detachable interlocking of said panels.

* * * * *